United States Patent [19]

Kwok

[11] Patent Number: 4,944,901
[45] Date of Patent: Jul. 31, 1990

[54] METHOD OF MAKING DENTAL COPINGS

[76] Inventor: Lloyd A. Kwok, 6170 Skyline Blvd., Burlingame, Calif. 94010

[21] Appl. No.: 181,569

[22] Filed: Apr. 14, 1988

[51] Int. Cl.$^5$ .................. A61C 13/08; B29C 51/10; B29C 51/18
[52] U.S. Cl. .................. 264/19; 264/554; 425/388
[58] Field of Search .................. 264/16–19, 264/554; 425/388

[56] References Cited

U.S. PATENT DOCUMENTS

| | | | |
|---|---|---|---|
| 3,021,569 | 2/1962 | Lyman | 264/554 X |
| 3,270,104 | 8/1966 | Dreyfus et al. | 264/554 |
| 3,404,056 | 10/1968 | Baldwin | 264/554 X |
| 3,467,741 | 9/1969 | Kesling | 264/554 X |
| 3,532,776 | 10/1970 | Kopp | 264/554 X |
| 3,643,730 | 2/1972 | Scheu | 264/554 X |
| 3,682,571 | 8/1972 | Greenberg et al. | 264/554 X |
| 3,682,580 | 8/1972 | Greenberg et al. | 264/554 X |
| 3,724,673 | 4/1973 | Ryon | 264/554 X |
| 3,880,563 | 4/1975 | De Vos | 425/388 X |
| 3,955,266 | 5/1976 | Horami et al. | 425/388 X |
| 4,270,892 | 6/1981 | Faunce | 264/554 X |
| 4,567,932 | 2/1986 | Hollenbach | 425/388 X |

FOREIGN PATENT DOCUMENTS

| | | | |
|---|---|---|---|
| 1104821 | 5/1986 | Japan | 425/388 |
| 1104822 | 5/1986 | Japan | 425/388 |
| 2039218 | 2/1987 | Japan | 425/388 |

Primary Examiner—Jan H. Silbaugh
Assistant Examiner—Karen D. Kutach
Attorney, Agent, or Firm—Thomas M. Freiburger

[57] ABSTRACT

A method for producing dental copings using a vacuum tray permits the making of a large number of copings simultaneously using a single sheet of plastic material. Vacuum is applied to the perforated bottom of a box-like tray partially filled with a die retaining medium such as lead shot. Dies are held in position by being embedded in the lead shot and extending above the lead shot. A frame holds a sheet of heat-softenable plastic material, which is heated from above. The frame is lowered onto the shot-containing tray and the vacuum draws the heat-softened plastic material down over the field of dies, producing copings on all the dies simultaneously.

8 Claims, 2 Drawing Sheets

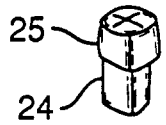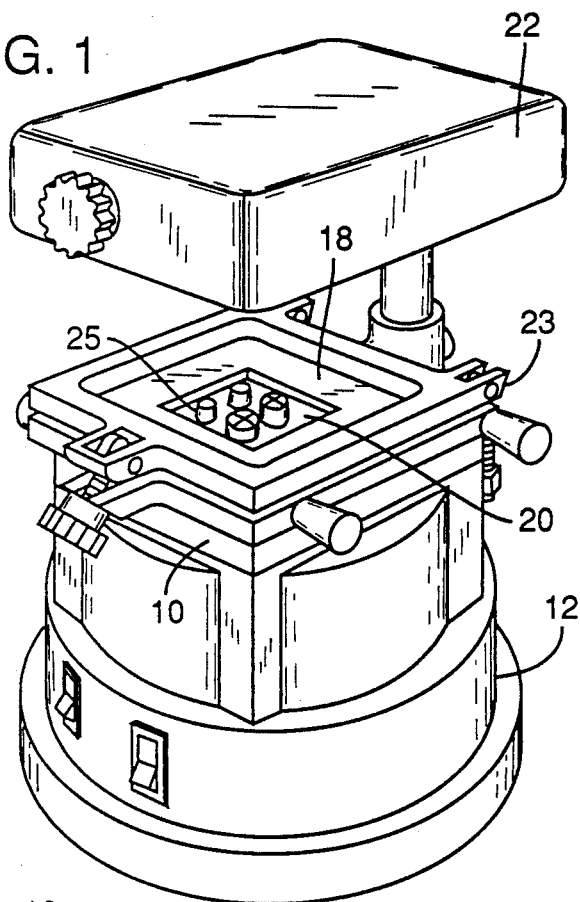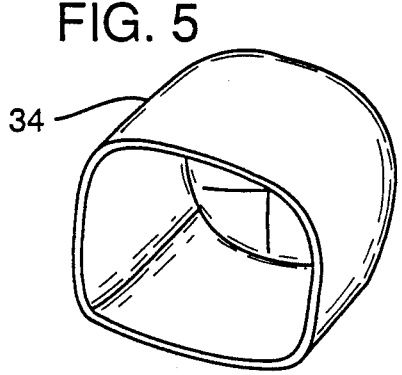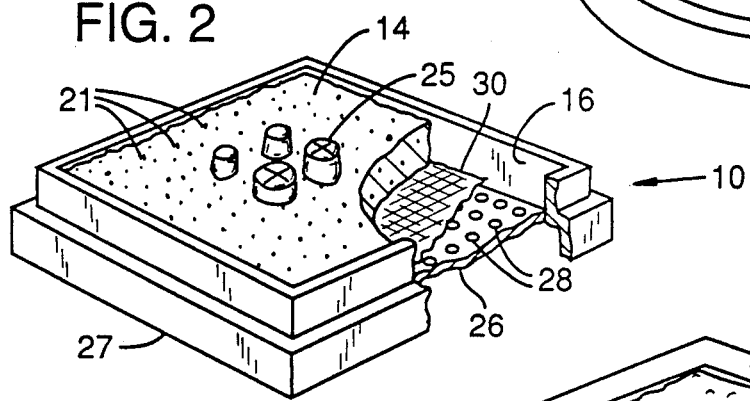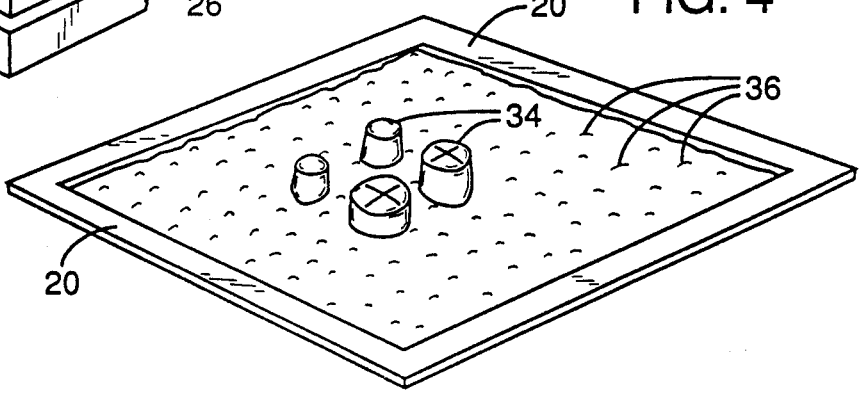

METHOD OF MAKING DENTAL COPINGS

BACKGROUND OF THE INVENTION

The invention relates to dental apparatus and methods, and more particularly to a method and system for producing a plurality of dental copings simultaneously.

Dental copings, for example for crowns and bridges, have been made in several different ways. They have conventionally been produced from wax warmed and softened in a warm water bath and vacuum formed on dies of the tooth or teeth. They have also been formed by manual application of molten wax on the dies via a spatula. Dies have also been dipped in molten wax held in a container.

However, when a wax coping is removed from a die, it must be handled with extreme care to avoid deformation of the coping, which would destroy the coping. Also, prominent points on a die covered with wax tend to poke through the wax, forming a defective coping.

Wax copings have generally been produced one at a time, by pushing the softened wax or a putty-like thin sheet of material by hand down over the die.

Thin sheets of relatively rigid plastic material in different thicknesses have been used previously to produce some full-mouth dental appliances such as night guards, custom trays, etc. but not to produce accurate copings.

Previous apparatus and processes for producing dental copings were not capable of efficient and reliable production of a plurality of dental copings simultaneously. Such procedures were also not capable of producing a substantially rigid coping which retains its shape, and these are objects of the present invention as described below.

SUMMARY OF THE INVENTION

In accordance with the present invention, a number of dental copings may be produced simultaneously from a substantially rigid-setting plastic material which, even if deformed, will regain its shape.

A coping retaining tray, which may be box-like in shape, has a bottom preferably shaped to fit over a standard vacuum platform of a vacuum forming machine. The tray has a recess or well with a perforated bottom, i.e. a multiplicity of holes through which vacuum is communicated to the recess or well.

Contained within the recess or well is a die retention medium comprising a fluid-like mass through which vacuum can be communicated. The medium preferably comprises a bed of small spherical members, which may advantageously be lead shot, preferably number 9 hard lead shot, for example. Between the perforated tray bottom and the lead shot is interposed some means for preventing the blockage of the vacuum holes by the shot, and this may comprise a screen or wire mesh. Two layers of mesh can be used, although one is ordinarily sufficient.

Dental dies, for example dies in the shape of individual prepared teeth and having some form of tail piece or pin extending down from them, are positioned with the tail piece in the die retention medium, i.e. the mass of spherical members, such that the spherical members hold the dies upright and steadily in the tray. The portion of the die to be coped extends above the mass. A large number of dies (i.e. six to 12) may be retained with relatively small spacing between them, i.e. about one-fourth inch minimum spacing.

A sheet of thermally-softenable plastic material such as polypropylene is retained in a frame or sandwiched template configured to overlay the top of the tray. The frame has a "window" or opening which exposes the sheet of plastic material to the dies. The window or opening, and thus the usable portion of the plastic material, is large enough to cover all of the dies contained in the tray for the particular operation being conducted. Smaller sheets of plastic and frames with smaller openings may be used when fewer dies are placed in the tray.

Heat is applied from above the sheet of plastic material, and at the same time, vacuum is applied from below the tray. The heating element may be a resistance heater, an ultrasonic source, or other suitable heating device.

The vacuum communicated from the source up through the fluid-like mass of spherical members draws the softened sheet of plastic material down against and tightly over the dies, to produce simultaneously a plurality of copings, one on each die. The softened plastic is drawn into contact substantially completely over the important surfaces of each die, producing a high quality coping.

The heat and vacuum are removed, and the copings may then be removed from the dies. The sheet of plastic is cut around each coping, to separate the individual copings.

It is therefore among the objects of the invention to provide an improved method and apparatus for producing a plurality of dental copings simultaneously, from a superior material, and to produce the copings quickly, efficiently and reliably. These and other objects, advantages and features of the invention will be apparent from the following description of a preferred embodiment, considered along with the accompanying drawings.

DESCRIPTION OF THE DRAWINGS

FIG. 1 is a perspective view illustrating the system and method of the invention.

FIG. 2 is a perspective view illustrating in greater detail a tray for holding dental copings in accordance with the method and system of the invention. Dental dies are shown retained in the tray, held firmly in place by a mass of lead shot. Portions of the tray and of the lead shot are reused in FIG. 2 to illustrate structural features.

FIG. 3 is a perspective view showing an individual die with a tail piece or pin.

FIG. 4 is a perspective view indicating the deformation of a sheet of heat-softened plastic material over several dies.

FIG. 5 is a perspective view showing a finished dental coping formed of relatively rigid plastic material by the method and system of the invention.

DESCRIPTION OF PREFERRED EMBODIMENT

Figure 6:
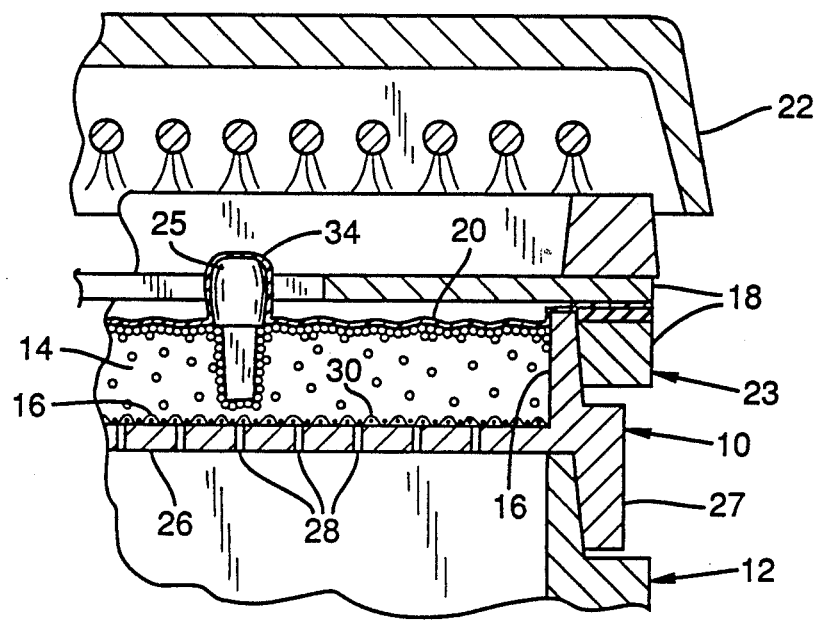
FIG. 6 is a partial cross-sectional view showing heat being applied to form dental copings on dies held in the tray.

In the drawings, FIGS. 1-6 illustrate the method and system of the invention. The system includes a vacuum tray or die holding tray 10 supported on a vacuum forming machine or vacuum platform 12 having a source of vacuum, a die holding medium 14 contained in a recess or well 16 of the tray, a retention frame 18 for holding a piece of semi-rigid heat softenable plastic material 20, and a heating device 22 positioned above the frame and plastic sheet. The plastic sheet holder frame 18 may be retained in a retaining device 23, as illustrated in FIGS. 1 and 6.

As shown particularly in FIG. 2, the die holding medium 14 preferably comprises a fluid-like mass of small spherical members 21, preferably lead shot which may be in the range of 1.5 to 2.5 mm in diameter (number 9 lead shot, for example). The heavy lead shot has the ability to securely retain a tail extension or pin 24 (FIG. 3) of a dental die 25, with the desired portion of the die extending above the lead shot mass as shown in FIGS. 1 and 2. The dies can be easily pushed into the fluid-like mass 14 of lead shot, and they will remain in the same position through the procedure of forming copings.

A plurality of the dies 25 are pushed into the retaining medium, e.g. the lead shot mass 14 as illustrated. The portions of the dies to be coped extend above the mass as shown. When these dies are all in place, the frame 18, which may be a sandwiched template, is closed on a sheet of plastic material 20. This material may be, for example, polypropylene, about 0.3 to 0.5 mm thick (preferably about 0.4 mm). The plastic material is heat-softenable preferably at a temperature of about 120° to 135° F., preferably about 128° F. When formed into a small three-dimensional structure such as a dental coping of a tooth or teeth, the plastic material is relatively rigid, yet flexible enough to enable the release of the die from the finished coping without permanent deformation of the coping.

FIG. 2 shows the die holding tray 10 with a multiplicity of holes 28 through its bottom 26 for communicating vacuum from the vacuum platform 12 to the recess or well 16 of the tray. To prevent the vacuum holes from being covered or substantially being covered by the spherical members, drawn against the holes by vacuum such that vacuum might be substantially shut off, a screen or wire mesh 30 preferably is positioned at the inside bottom of the tray recess. The mesh 30 has openings which are smaller than the diameter of the spherical members 14, so that the spherical members are held above the vacuum holes in the tray bottom.

The tray bottom 26 preferably has a peripheral flange 27 extending downwardly to form a box-like recess at the bottom side of the tray. This recess and the flange 27 are sized and configured to fit essentially in sealed relationship on a standard vacuum platform. The base defined by the flange 27 may be about 5 inches square, for example.

FIG. 4 shows the sheet of plastic material 20 after it has been vacuum drawn down onto the dies 25 in a heat-softened condition in accordance with the method of the invention. The article depicted in FIG. 4 is a single, solid, integral piece of formed plastic material 20. This is also seen in the cross-sectional view of FIG. 6, where the formed plastic sheet 20 still remains over the tray 10. As indicated, a plurality of copings 34 are formed in the sheet of plastic material, each conforming substantially to the shape of a die which was retained in the retaining medium, i.e. the mass of lead shot 14. Bumps 36 are shown formed in the sheet 20 by the surface of the mass of spherical members 21.

Many of the copings will retain a grip on the corresponding die, wrapping around and somewhat under the die, when the sheet of plastic 20 has been removed from the frame 18 and holding tray 10. The plastic material, though semi-rigid particularly when formed into the relatively small dimensions of a coping, is pliable enough that the die can be pushed out of the coping. Although this requires a slight deformation of the coping, the plastic material of the coping regains its shape once the die has been removed.

The individual copings are cut from the sheet of plastic material, and an example of a finished coping is shown in FIG. 5.

By the method and apparatus of the invention, dental copings are quickly and inexpensively formed of an advantageous semi-rigid plastic material. The time involved in producing a dozen copings, for example, is greatly reduced as compared to prior practice in producing dental copings. The die holding tray fits a standard vacuum platform or vacuum former as used in dental laboratories.

The above described preferred embodiment is intended to illustrate the principles of the invention but not to limit its scope. Other embodiments and variations to this preferred embodiment will be apparent to those skilled in the art and may be made without departing from scope of the invention as defined in the following claims.

I claim:

1. A method for producing a plurality of dental copings simultaneously, comprising,
    providing a die-holding tray having a well or recess, the tray having a plurality of holes through its bottom communicating with the well or recess,
    preventing blockage of the holes by positioning a wire mesh over the holes in the bottom of the well or recess,
    partially filling the well or recess with a fluid-like mass of lead shot over the wire mesh,
    placing a plurality of dental dies, each having a tail piece or pin, into the fluid-like mass of lead shot such that the tail pieces or pins on the dies are submerged into the fluid-like mass of lead shot and held in position by the lead shot, serving as a die holding medium,
    laying a sheet of heat-softenable plastic material, retained in a frame, over the top of the tray so as to cover the recess or well, substantially sealing against air leakage into the well or recess,
    applying heat to the sheet from above, to soften the sheet to the extent that it can be deformed into dental copings around the dies,
    applying a source of vacuum to the bottom side of the tray so as to apply vacuum to the well or recess up through the fluid-like mass of lead shot and thereby drawing the softened sheet down around the dies using the vacuum to deform the sheet into dental copings, and
    removing the heat after the copings have properly formed over the dies, and allowing the copings to cool.

2. The method of claim 1, wherein the lead shot is in the range of 1.5 to 2.5 mm in diameter.

3. The method of claim 1, wherein the lead shot comprises substantially number 9 hard lead shot.

4. The method of claim 1, wherein the plastic material comprises polypropylene.

5. The method of claim 4, wherein the sheet of plastic material is about 0.4 mm thick.

6. The method of claim 1, wherein the step of applying a vacuum to the tray comprises placing the tray on a vacuum stand in such a way that air leakage is substantially prevented between the vacuum stand and the tray.

7. The method of claim 1, wherein heat is applied to bring the temperature of the sheet of plastic material to about 128° F.

8. The method of claim 1, wherein the step of laying the sheet of heat-softenable plastic material over the top of the tray comprises using as the frame a sandwich type template having two plates with an opening, and sandwiching the sheet of plastic material between the two plates so as to expose a portion of the sheet of plastic material, and engaging one of the plates of the template against the top of the tray in such a way as to substantially seal against air leakage.

* * * * *